United States Patent [19]

Olah

[11] Patent Number: 5,073,674

[45] Date of Patent: Dec. 17, 1991

[54] ENVIRONMENTALLY SAFE CATALYTIC ALKYATION USING LIQUID ONIUM POLY (HYDROGEN FLUORIDES)

[76] Inventor: George A. Olah, 2252 Gloaming Way, Beverly Hills, Calif. 90210

[21] Appl. No.: 585,540

[22] Filed: Sep. 20, 1990

Related U.S. Application Data

[63] Continuation-in-part of Ser. No. 511,655, Apr. 20, 1990, abandoned.

[51] Int. Cl.⁵ ............................ C07C 2/68; C07C 2/70
[52] U.S. Cl. .................................. 585/725; 585/721; 585/723
[58] Field of Search ............... 585/709, 710, 721, 723, 585/724, 725

[56] References Cited

U.S. PATENT DOCUMENTS

| | | | |
|---|---|---|---|
| 3,888,935 | 6/1975 | Sobel | 585/723 |
| 4,065,405 | 12/1977 | Holme | 585/710 |
| 4,071,576 | 1/1978 | Behrmann et al. | 585/70 |
| 4,096,197 | 6/1978 | Mayer | 585/710 |
| 4,544,794 | 10/1985 | Miller et al. | 585/721 |
| 4,547,474 | 10/1985 | Olah | 502/168 |
| 4,663,026 | 5/1987 | Louie et al. | 585/723 |
| 4,783,567 | 11/1988 | Kocal | 585/723 |
| 4,891,466 | 1/1990 | Koral | 585/725 |
| 4,962,268 | 10/1990 | Hovis | 585/709 |

FOREIGN PATENT DOCUMENTS 0243923 3/1987 Fed. Rep. of Germany ...... 585/725

OTHER PUBLICATIONS

Hirschmann et al., "The Reaction of Epoxides with Anhydrous Hydrogen Fluoride in the Presence of Organic Bases. The Preparation of 9-Fluoro-4-Pregnene-11,17,21-Triol 3,20-Dione 21-Acetate and its 1-Dehydro Analog." Journal of the American Chemical Society 78:4956-4959 (1956).

Olah G. et al., "Synthetic Methods and Reactions, 63, Pyridinium Poly(hydrogen fluoride) (30% Pyridine-70% Hydrogen Fluoride): A Convenient Reagent for Organic Fluorination Reactions," Journal of Organic Chemistry 44/22:3872-3881 (1979).

Bergstrom et al., "9-Fluoro-11-Deoxy Steroids," Journal of Organic Chemistry 28:2633-2640 (1963).

Fukuhara et al., "Melamine-Anhydrous Hydrogen Fluoride Solution as a Highly Effective and Convenient Hydrofluorination Reagent," The Chemical Society of Japan 10:1951-1957 (1985).

*Primary Examiner*—Anthony McFarlane
*Attorney, Agent, or Firm*—Pennie & Edmonds

[57] ABSTRACT

A process for alkylating an aliphatic hydrocarbon having isobutane with an alkenyl hydrocarbon with isobutylene in the presence of a liquid onium polyhydrogen fluoride complex as the reaction medium and catalyst at a temperature between −20° and 70° and pressure between atmospheric and 200 psi and at a time sufficient to form a high octane alkylate thereof.

20 Claims, No Drawings

5,073,674

ENVIRONMENTALLY SAFE CATALYTIC ALKYATION USING LIQUID ONIUM POLY (HYDROGEN FLUORIDES)

This application is a continuation-in-part of application Ser. No. 07/511,655 filed Apr. 20, 1990, now abandoned.

BACKGROUND OF THE INVENTION

Anhydrous hydrogen fluoride is widely used as a catalyst in the petrochemical industry. It is particularly effective as an alkylation catalyst, such as in the production of high octane gasoline via the isobutane-isobutylene alkylation reaction. This technology has achieved significant application in refineries. At the same time, because of the volatility of hydrogen fluoride (bp. 19.6° C.), the environmental danger in case of accidental release from industrial reactors or storage tanks to the atmosphere is increasingly unacceptable. To solve this problem, industry has mostly reverted either to the use of sulfuric acid, a less suitable alkylation catalyst which, however, is nonvolatile under most operating conditions, or has operated in a manner which decreases or minimizes the volatility of the hydrogen fluoride catalyst systems.

Certain polyhydrogen fluoride complexes, such as those of pyridine, are known and used as fluorinating agents. Anhydrous hydrogen fluoride in the presence of pyridine has been used for fluorinating steroids (R. R. Hirschmann et al., J. Am. Chem. Soc. 78, 1956, p. 4956). The 30% pyridine-70% hydrogen fluoride system was found to be particularly useful for this reaction (C. G. Bergstrom et al., J. Org. Chem. 28, 1963, p. 2633) and subsequently was developed by Olah et al., J. Org. Chem. 44, 1979, p. 3872 and references cited therein). The use of the reagent for a wide variety of fluorination reactions has been explored. The PPHF reagent and subsequently developed related reagents (T. Fukuhara, et al., Nippon Kagaku Kaish, 1985, p. 1951) were only recognized as convenient fluorinating agents. These reagents have not been previously utilized as alkylation catalysts.

SUMMARY OF THE INVENTION

The present invention relates to a process for alkylating an aliphatic hydrocarbon having between three and twelve carbon atoms and optionally containing an alkyl group of between one and four carbon atoms, with an alkenyl hydrocarbon having between two and twelve carbon atoms optionally containing an alkyl group of between one and four carbon atoms, in the presence of a liquid onium polyhydrogen fluoride complex as the reaction medium and catalyst at a sufficient temperature and pressure and at a time sufficient to form an alkylate thereof.

In the process of the invention, the temperature is preferably maintained at between −20° and 70° C. and the pressure used is between atmospheric and 200 psi. The preferred polyhydrogen fluoride complexes are those of ammonia, methylamines, ethylamines, propylamines, butylamines, pentylamines, pyridine, picoline, melamine, hexamethylene-tetramine and the like. These complexes preferably contain about 70 to 95% by weight anhydrous hydrogen fluoride, with the amine component being present in an amount of between 5% and 30% by weight.

Advantageously, the reaction is conducted batchwise or under continuous flow conditions, with an aliphatic hydrocarbon to alkenyl hydrocarbon weight ratio of between about 2:1 to 10:1. Higher yields can be obtained by adding the alkenyl hydrocarbon in portions to a mixture of the aliphatic hydrocarbon and the catalyst complex.

In this process, beneficial results can be obtained by adding a co-catalyst to the reaction mixture. The preferred co-catalysts are one of a Lewis acid halide, a perfluorosulfonate, or a perfluoroalkanesulfonic acid. These materials are disclosed in U.S. Pat. No. 4,547,474, the content of which is expressly incorporated by reference herein. The co-catalyst is present in an amount of between about 0.1 to 10% by weight of the reaction mixture.

A preferred embodiment of the invention relates to process for alkylating an aliphatic hydrocarbon such as isobutane with an alkenyl hydrocarbon such as isobutylene in the presence of a liquid onium polyhydrogen fluoride complex as the reaction medium and catalyst at a temperature between −20° and 70° C. and pressure between atmospheric and 200 psi for a time sufficient to form a high octane alkylate thereof.

DETAILED DESCRIPTION OF THE INVENTION

The present invention relates to the discovery that the volatility of anhydrous hydrogen fluoride catalysts can be substantially decreased or eliminated by using suitable liquid ammonia or amine polyhydrogen fluoride complexes containing between about 70 to 95% by weight hydrogen fluoride.

The use of such liquid hydrogen fluoride complexes as catalysts in alkylation reactions is unexpected and unprecedented. Acidic metal hydrogen fluorides of the type $M^+HF_2$ or simple HF salts of amines show no catalytic activity in alkylation reactions, such as that of isobutane with isobutylene. In sharp contrast, when isobutane and isobutylene are reacted in ammonia poly(hydrogen fluoride), for example, which is composed of 30% to 5% by weight of ammonia and which shows little or no decomposition below 50° C., alkylation readily takes place.

The use of the stable, liquid polyhydrogen fluoride complexes as the catalytic medium to effect alkylation represents significant advantages. Due to the substantially reduced volatility of the hydrogen fluoride complex, atmospheric release, in sharp contrast to hydrogen fluoride itself, represents a vastly decreased degree of hazard. The liquid polyhydrogen fluorides can be efficiently diluted with water and neutralized with caustic treatment without forming dangerous aerosols characteristic of gaseous HF release. Also, because of their low vapor pressure of below 35°–50° C., the operating pressures in the alkylation reactors and storage tanks are substantially decreased.

A further aspect of the invention is that onium polyhydrogen fluoride complexes can also be treated with small (0.1 to 10% by weight) amounts of Lewis acid halide (preferentially fluoride) or perfluoroalkanesulfonate co-catalysts to further enhance their activity. Such Lewis acids are particularly those of elements of the groups IIIa and Va of the periodic table. Especially boron trifluoride, boron tristriflate, antimony pentafluoride, arsenic pentafluoride, phosphorus pentafluoride, tantalum pentafluoride, niobium pentafluoride and the like are effective. Conjugate superacids are formed in the polyhydrogen fluoride media, which themselves are non-volatile and thus environmentally safe. Adding similar amounts of any strong Bronstead acid, such as perfluoroalkanesulfonic acids for example, to the media also provides enhanced catalytic activity for such alkylations.

The invention is particularly advantageous to minimize or eliminate environmental hazards associated with the use of anhydrous hydrogen fluoride in industrial alkylation plants. Further, the new nonvolatile complexed hydrogen fluoride technology is directly applicable to existing plant equipment and thus its industrial use does not involve costly process changes or any major changes in operating technology.

EXAMPLES

The following examples are typical, but by no means are they to be construed as limiting the scope of the new alkylation technology of the present invention using polyhydrogen fluorides with greatly decreased volatility as catalysts.

Example 1

A 250 ml stainless steel pressure reaction vessel was charged with 15 ml of isobutylene and 100 ml of isobutane. 60 ml of a liquid pyridinium polyhydrogen fluoride complex $(Py(HF)_a)$, the composition containing 20% by weight pyridine and 80% by weight anhydrous hydrogen fluoride, was then introduced and the reaction mixture stirred for 30 minutes while keeping the temperature below 40°-45° C. After depressurizing workup involving an alkaline wash gave 24 ml of hydrocarbon alkylate containing 71% of octanes, including 40% isooctane and related isomeric alkanes, as well as related olefin oligomers (results analyzed by gas-liquid chromatography and mass spectrometry).

Example 2

The reaction was carried out as in Example 1 but the reaction time was prolonged to 16 hrs. No significant change in the product distribution was observed from that of Example 1.

Example 3

The reaction was carried out as in Example 1. Isobutylene was fed in portions to the reaction vessel containing pyridinium poly(hydrogen fluoride) and isobutane. The alkylate product formed in this manner contained less than 5% of olefin oligomers.

Example 4

An alkylation was carried out as in the previous examples but 10% by weight boron trifluoride was added to the reaction mixture. This material dissolves in the polyhydrogen fluoride complex, thus forming a stable complexed superacid. The alkylation reaction was carried out for a period of 20 minutes and resulted in the formation of alkylation products comparable to Example 1.

Example 5

The reaction was carried out as in Example 1, but using a liquid ammonium poly(hydrogen fluoride) complex composed of 10% by weight ammonium fluoride and 90% by weight hydrogen fluoride. The weight ratio of isobutane in relation to isobutylene was 6:1. After workup, including removal of excess isobutane for recycling. 25 ml of alkylate was obtained containing 84% of octanes in general and 51% of isooctane in particular.

Example 6

The reaction was carried out as in previous Example, but using a 85:15 weight ratio mixture of anhydrous hydrogen fluoride and melamine. 26 ml of alkylate containing 91% of octanes (with 50% isooctane) was obtained.

What is claimed is:

1. A process for alkylating an aliphatic hydrocarbon having between three and twelve carbon atoms and optionally containing an alkyl group of between one and four carbon atoms, with an alkenyl hydrocarbon having between two and twelve carbon atoms and optionally containing an alkyl group of between one and four carbon atoms, in the presence of a liquid onium polyhydrogen fluoride complex as the reaction medium and catalyst at a sufficient temperature pressure and time to form an alkylate thereof.

2. The process of claim 1 wherein the temperature is between $-20°$ and 70° C., and the pressure is between atmospheric and 200 psi.

3. The process of claim 1 wherein the reaction is conducted batchwise or under continuous flow conditions.

4. The process of claim 1 wherein the weight ratio of aliphatic hydrocarbon to alkenyl hydrocarbon ranges from about 2:1 to 10:1.

5. The process of claim 1 wherein the polyhydrogen fluoride complex is a complex of ammonium, methylamine, ethylamine, propylamine, butylamine, pentylamine, pyridine, picoline, triethanolamine, melamine, or hexamethylenetetramine in an amount of between about 5 and 30% by weight, and between about 70 and 95% by weight hydrogen fluoride.

6. The process of claim 1 wherein the alkenyl compound is added in portions to a mixture of the aliphatic hydrocarbon and catalyst complex.

7. The process of claim 1 which further comprises adding a co-catalyst to the reaction mixture.

8. The process of claim 7 wherein the co-catalyst is a Lewis acid halide, a perfluorosulfonate, or a perfluoroalkane sulfonic acid.

9. The process of claim 7 wherein the co-catalyst is present in an amount of between about 0.1 to 10% by weight of the reaction mixture.

10. A process for alkylating isobutane with isobutylene in the presence of liquid onium polyhydrogen fluoride complex as the reaction medium and catalyst at a temperature of between $-20°$ and 70° C. and a pressure between atmospheric and 200 psi for a time sufficient to form a high octane alkylate thereof.

11. The process of claim 10 wherein the isobutylene is added in portions to a mixture of the isobutane and catalyst complex.

12. The process of claim 11 wherein the reaction is conducted batchwise or under continuous flow conditions with an isobutane/isobutylene weight ratio ranging from about 2:1 to 10:1.

13. The process of claim 12 wherein the polyhydrogen fluoride complex is a complex of ammonium, methylamine, ethylamine, propylamine, butylamine, pentylamine, pyridine, picoline, triethanolamine, melamine, or hexamethylenetetramine in an amount of between about 5 and 30% by weight and between about 70 and 95% by weight hydrogen fluoride.

14. The process of claim 10 which further comprises adding a co-catalyst to the reaction mixture.

15. The process of claim 14 wherein the co-catalyst is a Lewis acid halide, a perfluorosulfonate, or a perfluoroalkane sulfonic acid.

16. The process of claim 15 wherein the co-catalyst is present in an amount of between about 0.1 to 10% by weight of the reaction mixture.

17. A process for alkylating an aliphatic hydrocarbon having between three and twelve carbon atoms and optionally containing an alkyl group of between one and four carbon atoms, with an alkenyl hydrocarbon having between two and twelve carbon atoms and optionally containing an alkyl group of between one and four carbon atoms, wherein the weight ratio of aliphatic hydrocarbon to alkenyl hydrocarbon is between about 2:1 to 10:1 in the presence of a liquid onium polyhydrogen fluoride complex of ammonia, pyridine, picoline, methylamine, ethylamine, propylamine, butylamine, triethanolamine, melamine, or hexamethylene tetramine in an amount of between about 5 to 30% by weight and hydrogen fluoride in an amount of between about 70 to 95% by weight as a reaction medium and catalyst at a sufficient temperature and pressure and for a sufficient time to form an alkylate thereof.

18. The process of claim 17 wherein the reaction is conducted batchwise or under continuous flow conditions.

19. The process of claim 18 further comprising a co-catalyst in an amount of 0.1 to 10% by weight of the reaction mixture.

20. The process of claim 19 wherein the co-catalyst is a Lewis acid halide, a perfluorosulfonate, or a perfluoroalkanesulfonic acid.

* * * * *